United States Patent
Xu et al.

(10) Patent No.: US 7,902,253 B2
(45) Date of Patent: Mar. 8, 2011

(54) ISOFLAVONE DERIVATIVES OF TECTORIGENIN, THE PREPARATION THEREOF AND THE ANTIVIRAL MEDICINE CONTAINING THE SAME AS AN EFFECTIVE CONSTITUENT

(75) Inventors: Xuemin Xu, Sichuan (CN); Chongjun Yuan, Sichuan (CN); Jia Wang, Sichuan (CN); Shangbin Qi, Sichuan (CN); Hai Yin, Sichuan (CN); Yanming Zeng, Sichuan (CN)

(73) Assignees: Chengdu Dikang Pharmaceutical Institute, Sichuan (CN); Sichuan Dikang Sci-Tech Pharmaceutical Co., Ltd., Sichuan (CN)

( * ) Notice: Subject to any disclaimer, the term of this patent is extended or adjusted under 35 U.S.C. 154(b) by 1055 days.

(21) Appl. No.: 10/556,776

(22) PCT Filed: May 14, 2004

(86) PCT No.: PCT/CN2004/000481
§ 371 (c)(1),
(2), (4) Date: Nov. 17, 2006

(87) PCT Pub. No.: WO2004/111027
PCT Pub. Date: Dec. 23, 2004

(65) Prior Publication Data
US 2007/0123566 A1 May 31, 2007

(30) Foreign Application Priority Data
May 15, 2003 (CN) ................................. 03 1 17865

(51) Int. Cl.
A61K 31/452 (2006.01)
C07D 405/01 (2006.01)
(52) U.S. Cl. .......... 514/456; 514/320; 546/196; 549/403
(58) Field of Classification Search .................. 514/403, 514/320, 456; 549/403
See application file for complete search history.

(56) References Cited

U.S. PATENT DOCUMENTS
| | | | |
|---|---|---|---|
| 4,352,792 A | 10/1982 | Ishitsuka et al. | 422/179 |
| 4,772,627 A | 9/1988 | Matsui et al. | 514/462 |
| 6,541,613 B2 | 4/2003 | Hendler et al. | 536/8 |
| 2005/0037100 A1 * | 2/2005 | Wuttke et al. | 424/764 |

FOREIGN PATENT DOCUMENTS
WO WO9947149 * 9/1999

OTHER PUBLICATIONS

Qin et al. "Pharmacokinetics of tectorigenin . . ." CA 150:136024 (2008).*
Zhang et al. "Identicication of the major . . ." Rapid. Comm. Mass Spect. v.22, p. 2677-2684 (2008).*
Tsuchiya et al. "Allergy inhibitors . . ." CA 109:216001 (1988).*
Matsuda et al. "Isoflavone . . ." CA 104:147153 (1986).*
Wu, Y.X.; Xu, L.X.; Analysis of isoflavones in *Belamcanda chinesis* (L.) DC. and *Iris lectorum* Maxim by square wave voltammetry; Yaoxue Xuebao, 27(1), 64-8 (Chinese) 1992; American Chemical Society 1997; Chemistry Abstract vol. 116:191100.

* cited by examiner

Primary Examiner — Celia Chang
(74) Attorney, Agent, or Firm — Greer, Burns & Crain, Ltd.

(57) ABSTRACT

An isoflavone derivative of tectorigenin compound as shown in formula (II), its preparation method and the antiviral medicine containing it as an effective constituent. The compound structure is shown as follows:

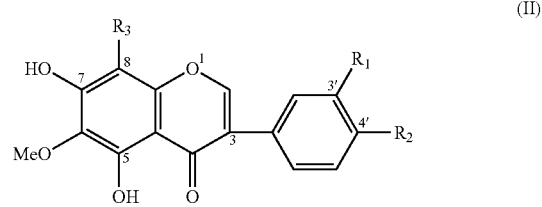

Where:: $R_1$ is H, $NH_2$ or $SO_3M$; $R_2$ is OR'; $R_3$ is H or $-CH_2NR''$; where R' is H, $-CH_2COONa$ or $-CH_2CH_2NMe_2$; NR" is

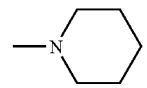

or $-NMe_2$; M is H, Na, K or $N^+H(CH_2CH_2OH)_3$.

10 Claims, 2 Drawing Sheets

ISOFLAVONE DERIVATIVES OF TECTORIGENIN, THE PREPARATION THEREOF AND THE ANTIVIRAL MEDICINE CONTAINING THE SAME AS AN EFFECTIVE CONSTITUENT

FIELD OF THE INVENTION

This invention relates to a derivative of tectorigenin compound, particularly speaking, it relates to a derivative of tectorigenin compound with chemical name is 5,7,4'-trihydroxy-6-methoxyl isoflavone). The present invention also relates to method for preparing the compound of the invention. The present invention also relates to an antiviral medicine containing the compound of the invention as an effective constituent.

BACKGROUND OF THE INVENTION

The diseases such as the upper respiratory tract infection and viral pneumonia caused by influenza virus and other many viruses infection are always the common and multiple diseases which could lead to death. The chemotherapy is still mainly used to cure such the respiratory tract infectious diseases. However, it has become a non-negligible question that growth speed of the drug-resistant bacterial strains and drug-resistant virus strains often exceeds the development of chemical antibiotic medicine. Attention is more and more paid to use and bring into full play the advantages of natural traditional Chinese medicine in this field, especially to extract and separate the effective pharmaceutical constituents from the natural medicines and/or to further develop and transform them into a new pharmaceutical compound on this basis.

As reported in many research reports and literatures such as Sun Yuanbiet al. (*Bulletin of the traditional Chinese medicine* 1984, 9 (5)), Cheng Fangqun (*Science of Chinese traditional and herbal drugs* 1990, 22 (2)), Xu Yunlong (*Plant research in Yunnan* 1999, 21, (1)), Ji Wenliang et al. (*Overseas medicineplant medicine part"* 2000, 15 (2) and *Chinese medical crop* 2000, 23 (8)), the tectorigenin compound as shown in formula (I) is an isoflavone one among many flavone compound constituents widely existing in traditional Chinese medicines, i.e. the *Iridaceae* family plants with antiviral, antibacterial and anti-inflammatory functions such as *Iris tectorum Maxim*, *Belamcanda chinensis* (L.) DC, *Iris dichotoma pall.*, *Iris japonica* and *I. Iris tectorum*.

(I)

The research results in many literatures such as the above-mentioned ones indicate that the isoflavone constituent contained in traditional Chinese medicine—*Iris tectorum Maxim* has the obvious antiviral and anti-inflammatory functions. The tectoridin is a main effective constituent in *Iris tectorum maxim* (its content is about 5%). Both its literature reports and pharmacological research indicate that it has rather stronger antiviral and anti-inflammatory functions. The literature and pharmacological research of the tectorigenin as shown in the above-mentioned formula (I) demonstrate that it has the stronger antiviral and anti-inflammatory functions as a hydrolysis product of tectoridin. However, the tectoridin and tectorigenin have an inferior water-solubility and their clinical application is limited, so that a question to be firstly solved is to improve and increase their water-solubility. The experimental result indicates that it is non-ideal to increase their water-solubility through preparation method and it is just a feasible measure to change their chemical structure by chemical modification of the tectoridin and tectorigenin so as to increase their water-solubility, strengthen their curative effect and expand their applicable medical preparation scope under the preconditions of maintaining and even increasing their pharmaceutical effect.

SUMMARY OR THE INVENTION

The present invention provides a series of derivatives achieved by chemical modification on the basis of the tectorigenin compound as shown in the above formula (I), the water-solubility of the compounds of the present invention could be greatly improved and increased under the preconditions of at least maintaining the original antibacterial, antiviral, anti-inflammatory and antipyretic-&-analgesic effects of tectorigenin. Therefore the present invention provides a great convenience for expanding pharmaceutical and clinical application scope of tectorigenin compound.

In addition, the present invention provides an antiviral medicine comprising the compounds of the present invention as the effective constituent, and especially provides an injection-type medicinal preparation containing the compounds of the present invention.

The tectorigenin derivative of the present invention, i.e. its chemical designation is 5,7,4'-trihydroxy-6-methoxyl isoflavone derivative, is shown in formula (II):

(II)

$R_1$, $R_3$, and $R'$ are not simultaneously H.
Where:
$R_1$ is H, $NH_2$ or $SO_3M$;
$R_2$ is OR';
$R_3$ is H or —$CH_2NR''$;
Where,
R' is H, —$CH_2COONa$ or —$CH_2CH_2NMe_2$;
NR" is or —$NMe_2$;
M is H, Na, K or $N^+H(CH_2CH_2OH)_3$

A typical compound in the compound as shown in the above-mentioned general formula (II) is a sulfonic acid compound wherein $R_1$ is $SO_3M"$, where M" can be H, Na, K or —$N^+H(CH_2CH_2OH)_3$, and its structure is shown in formula (III)

(III)

A typical compound in the compound as shown in the above-mentioned general formula (III) is a sulfonic acid or sulfonate compound, i.e. M" in $SO_3M"$ is H, Na or K and its structure is shown in formula (IV):

(IV)

Another typical compound in the compound as shown in the above-mentioned general formula (III) is that its sulfonic acid group $R_1$ is —$SO_3^-N^+H(CH_2CH_2OH)_3$ and its structure is shown in formula (V):

(V)

The general formula (II) said in the invention includes also a typical compound wherein $R_1$ is $NH_2$, $R_2$ is OH and $R_3$ is H and its structure is shown in formula (VI):

(VI)

Again another typical compound said in the general formula (II) in this invention is that its $R_1$ is H, $R_2$ is —$OCH_2COONa$ and $R_3$ is H and its structure is shown in formula (VII):

(VII)

In addition, again another typical compound said in the general formula (II) in this invention is that its $R_1$ and $R_3$ are H and $R_2$ is $OCH_2CH_2NMe_2$ in its structure in the formula (II) and its structure is shown in formula (VIII):

(VIII)

In addition, again another typical compound in the above-mentioned general formula (II) in this invention is that $R_1$ is H, $R_2$ is OH and $R_3$ is —$CH_2NR"$, where NR" is and its structure is shown in formula (IX):

(IX)

Besides, again another typical compound in the above-said general formula (II) in this invention is that $R_1$ is H, $R_2$ is OH and $R_3$ is —$CH_2NMe_2$ and its structure is shown in formula (X):

(X)

The compounds as shown in formulas (VI), (VIII), (IX) and (X) among all the above-mentioned typical compounds can also be a pharmaceutically acceptable salt compounds, for example the most commonly used corresponding hydrochloride compounds.

Taking the isoflavone compound of tectorigenin as shown in formula (I) as raw material, all the compounds as shown in the above-mentioned formula (II) for their different concrete substituent groups and/or substitution positions in the invention can be manufactured by use of the known similar substitution compound preparation principles and methods.

For example, the precursor compound used as a raw material for chemical modification in the invention, i.e. the tectorigenin isoflavone compound as shown in the above formula (I) can be more conveniently and easily achieved by extraction and separation from the above-mentioned many medicinal plants of *Iridaceae* family in a manner reported up to now, besides it can be manufactured by de novo synthesis. For example, an extraction manner which can be used for reference is:

The raw medicinal material *Iris tectorum Maxim* is dried, ground, coarsely screened (by mesh #20), put in an extractor, heated by 70% ethanol (its weight is four times of the drug) and recycled three times (an hour duration at each time) respectively, filtered while it is hot and its filtrate is collected. After the ethanol is recovered at reduced pressure a brown extractum-like extract with specific weight of 1.2 g/ml (50° C.) is obtained and its yield is 49-51% (by weight) of the raw medicinal material. The above-mentioned extract is agitated evenly after adding 95% ethanol into it, the suspension is precipitated and filtered, the filtrate is agitated evenly after adding 95% ethanol again in it, this operation is repeated twice until the filtrate becomes nearly colorless and the crude tectoridin is obtained. It is heated and recycled for an hour after adding 70% ethanol in it and kept at a standstill, a faint yellow sediment is released, filtered out and recrystallized twice by 70% ethanol, the colorless crystalline powdery tectoridin is achieved and its yield is 4.5% of the raw medicinal material quantity.

200 g tectoridin is put into a round bottom flask, agitated evenly after adding 2000 ml 50% ethanol into it, shaken evenly, heated and recycled for two hours after adding 200 ml concentrated hydrochloric acid, filtered while it is hot and then kept at a standstill and a faint yellow thin and slender acicular crystal is released. It is filtered, dissolved in 400 ml 95% ethanol, poured into 800 ml boiled water, cooled down and a faint yellow thin and slender acicular crystal is released. It is recrystallized once again after filtering, dried at reduced pressure at 60° C. 123 g refined isoflavone compound of tectorigenin as shown in formula (I) (a faint yellow thin and slender acicular crystal) is obtained, its yield is 3% of the drug quantity and its content is more than 98%.

As for the derivative as shown in formula (III), a substituted product wherein $R_1$ is $SO_3H$ can be generally achieved by sulfonating reaction of the isoflavone compound as shown in formula (I) by use of sulfuric acid. One of its optimization methods is: 1.0 g tectorigenin is taken, agitated until it is dissolved after adding 4.0 g concentrated sulfuric acid in it, it reacts for 1.5~2 hours at room temperature, the whole reaction process goes under the waterless conditions and a sulfonic acid derivative product as shown in formula (III) wherein M" is H is obtained.

After it is further treated by saturated saline aqueous solution such as NaCl or KCl etc., the corresponding sodium sulfonate or potassium sulfonate compound as shown in the above-mentioned formula (IV) is achieved. Its two-step synthesis line is as follows:

A method for preparation of the tectorigenin compound as shown in the above-mentioned formula (V): the isoflavone compound of tectorigenin as shown in formula (I) is used as raw material, mixed with concentrated sulfuric acid, heated and agitated from 40° C. to 90° C. (an optimum temperature is 60° C.), poured into the saturated sodium chloride, other alkali metal hydrochloride, hydrobromate or nitrate solution after cooling down, a 3'-sodium sulfonate intermediate product is obtained, it is suspended in ethanol solution and the strong-acid cation resin is added into it, it is agitated until it is completely dissolved at room temperature, triethanolamine is then added into it, the solvent is evaporated out at reduced pressure, the compound as shown in formula (V) is achieved and its synthesis line is as follows:

A method for preparation of the tectorigenin compound as shown in the above-mentioned formula (VI): the isoflavone compound of tectorigenin as shown in formula (I) can be taken as raw material, a 3'-nitro intermediate compound is obtained by adding drop wise the ethanol solution mixed with nitric acid and concentrated sulfuric acid mixture (i.e. (nitric acid+sulfuric acid)/ethanol)) while it is cooled down in ice bath, it is then dissolved in methanol, a 3'-amino-substituted compound (VI) is obtained by hydrogen catalytic reduction at atmospheric pressure, the corresponding salt compound as shown in formula (VI) can-be further achieved by reaction with a pharmaceutically acceptable acid and its synthesis line is as follows:

When the tectorigenin compound as shown in the above-mentioned formula (VI) is prepared, the isoflavone compound of tectorigenin as shown in formula (I) can be taken as raw material and dissolved in the butanone and DMF mixed solvent together with ethyl chloroacetate, waterless $K_2CO_3$ and a catalytic quantity of NaI are added into them, the mixture is agitated, recycled, cooled down to room temperature, its insoluble matter is filtered out, the filtrate is concentrated at reduced pressure, the residue is dissolved in an appropriate quantity of water, extracted by ethyl acetate and then water-washed, the solvent is concentrated at reduced pressure after drying, a 4'-ester-ether intermediate product is obtained by flash column separation, it is hydrolyzed completely at normal atmospheric temperature after its dissolution in methanol and adding drop wise NaOH aqueous solution while it is agitated, its pH value is regulated by acid to pH3~4, a flocculated sediment is obtained by evaporating out the methanol at reduced pressure, the compound (VII) (the sodium salt) is achieved by reaction with $NaHCO_3$ after water-washing, and its synthesis line is as follows:

In order to prepare the tectorigenin compound as shown in the above-mentioned formula(VIII), β-dimethylaminoethanol can be firstly added dropwise into dichlorosulfoxide and fiercely agitated at 0° C., the mixture is agitated and reacts at 35~50° C. after dropping and then recrystallized by use of waterless ethanol and an intermediate product—β-dimethylaminochloride hydrochloride A is obtained. The isoflavone compound of tectorigenin as shown in formula (I) is taken as raw material, dissolved in a solvent such as butanone, acetone, DMF, THF or dioxane, into it are added waterless $K_2CO_3$ or $Na_2CO_3$, DMF and a catalytic quantity of NaI, it is then heated up to recycling, the above-mentioned intermediate product A can be added into it in five batches every half an hour, it is recycled at about 80° C., checked by use of a thin laminate, filtered after cooling down, a stickum is obtained by the filtrate concentration at reduced pressure in a rotary evaporator, extracted by ethyl acetate after dilution by an appropriate quantity of water (about 10 times water by weight), the extract is dried after water-washing, the solvent is evaporated out, the compound (VIII) is obtained, the corresponding salt compound of it can be further achieved by reaction with a pharmaceutically acceptable acid and its synthesis line is as follows:

(VIII)

A method for preparation of the tectorigenin compound as shown in the above-mentioned formula (IX): the isoflavone compound of tectorigenin as shown in formula (I) can be used as raw material, mixed with 37% (by weight) formaldehyde solution, piperidine and one of the solvents such as dioxane, THF, methanol or ethanol, then the compound (IX) is obtained by its cooling down and filtering after recycling reaction. Moreover, the corresponding salt compound as shown in formula (III) can be achieved by reaction with a pharmaceutically-acceptable acid and its synthesis line is as follows:

The experimental result indicates that the position selectivity of above-mentioned reaction is very specific for completely achieving the reaction product on circle A of chemical structure and it is different from the position reported in literature and previously designed (on circle C). Thus the present invention provides a method for obtaining the derivates selectively on the circle A of chemical structure of tectorigenin isoflavone and it is favorable for examining the influence of its structure renovation on activity in an all-round way. However, the derivation is carried out mostly on circle C in other reactions. The tectorigenin compound as shown in the above-mentioned formula (X) can be achieved by use of the similar method on this basis. For example: the isoflavone compound of tectorigenin as shown in formula (I) is used 'as raw material, mixed with 37% (by weight) formaldehyde solution, dimethylaminohydrochloride and one of the solvents such as dioxane, THF, methanol or ethanol, cooled down after recycling reaction, the compound (X) is obtained by filtering and collecting the residue, the corresponding salt compound as shown in formula (III) can be further achieved by reaction with a pharmaceutically-acceptable acid and its synthesis line is as follows:

The corresponding pharmaceutical composition with antiviral function can be made from an effective dosage of the derivative of tectorigenin compound as shown in the above-mentioned formula (II) used as an effective medicinal constituent and the pharmaceutically-acceptable auxiliary additive constituents in a currently conventional preparation way. As for these above-said antiviral compositions, the above-said salt compounds are specially suitable for preparing the injection-type medicines with antiviral function since they are able to have a satisfactory water-solubility besides the oral preparations can be commonly obtained. For example, a contrast test of the above-mentioned typical compounds is carried out in accordance with the solubility test method in an example on page X, *Chinese Pharmacopeia*, book two, 2000 edition: the finely ground powder test sample is taken, put in a certain quantity of solvent 25° C.±2° C., the mixture is fiercely shaken every five minutes for 30 minutes and the test is judged according to various solution performance definitions in the *Pharmacopeia*. The result is shown in table 1.

TABLE 1

| The solution performance comparison test result | |
|---|---|
| Compound | Solute: water (mg/ml) |
| Compound (I) | 0.1 mg/ml |
| Compound (IV) | 67 mg/ml |
| Compound (V) | 70 mg/ml |
| Compound (VI) | 8 mg/ml |
| Compound (VII) | 15 mg/ml |
| Compound (VIII) | 10 mg/ml |
| Compound (IX) | 8 mg/ml |
| Compound (X) | 9 mg/ml |

The result in table 1 indicates that solubility of the chemically modified isoflavone compound of tectorigenin derivative (II) in many structural forms in this invention is greatly increased because of introduction of many easily salified and/or hydrophilic groups and this is favorable for its pharmaceutical and clinical application and also for increasing its in vivo absorption and bioavailability.

In order to further guarantee and increase the solution stability of the tectorigenin compound derivative as shown in the above-mentioned formula (II) in injection a solubilizing constituent acceptable in the injection medicine can also be used in a permitted quantity on this basis when the above-mentioned injection-type pharmaceutical preparations are manufactured. One of the convenient optimum ways which can be used for reference and are proved effective by the test result is that the glucose with a weight/volume ration of 2~15% of the total injection quantity is added into the said injection-type preparations as a solubilizer and the hydrogen bonds are formed by structural association of the polyhydroxy in glucose with the isoflavone as shown in formula (II), so that its solubility in water is greatly increased.

The tectorigenin sodium sulfonate as shown in the above-mentioned formula (IV) is taken as an example, its water-solubility is only 20 mg/ml (2%) at room temperature and it could not reach the pharmaceutical concentration; its water-solubility could be increased to 50~60 mg/ml after heating to 60~100° C. and the sediment is released again after cooling down to room temperature. However, it could be kept clear at room and low (0° C.~5° C.) temperature, also diluted by water or sugar saline water optionally and would not become turbid after 4% glucose is added into the injection. Therefore, it can not only be used for intramuscular injection, but also for intravenous injection when it is added into sugar and/or saline water. This just demonstrates that the glucose can also greatly increase the stability of pharmaceutical preparation for injection while water-solubility of the tectorigenin sodium sulfonate as shown in the above-mentioned formula (IV) is increased.

For example, a method in one of the examples for preparation of the injection medicine containing the above-mentioned isoflavone derivative of tectorigenin (II) as an effective pharmaceutical constituent is: 5~80 parts (by weight) of the tectorigenin derivative (II) and 20~150 parts (by weight) of the glucose for injection are dissolved in 700~800 parts (by weight) of water for injection, the water for injection is added in them after complete dissolution for making up to the total volume equivalent to 1000 parts (by weight) and a faint yellow transparent liquid injection containing 2~15% glucose and 5~80 mg/ml effective pharmaceutical constituent (i.e. compound (II)) is achieved after filtering by a G4 sintered glass funnel, conventional packing and sterilization.

The invention will be further described in detail in the following concrete examples. However, this should not be so understood that the invention theme is only limited in the following examples. Various substitutions and alterations made according to the common technical knowledge and conventional means in this field are all included in this invention scope without breaking away from the above-mentioned technological ideas in the invention.

DETAILED DESCRIPTION OF THE PREFERRED EMBODIMENTS

EXAMPLE 1

Preparation of Compound (IV)

Figure 1:
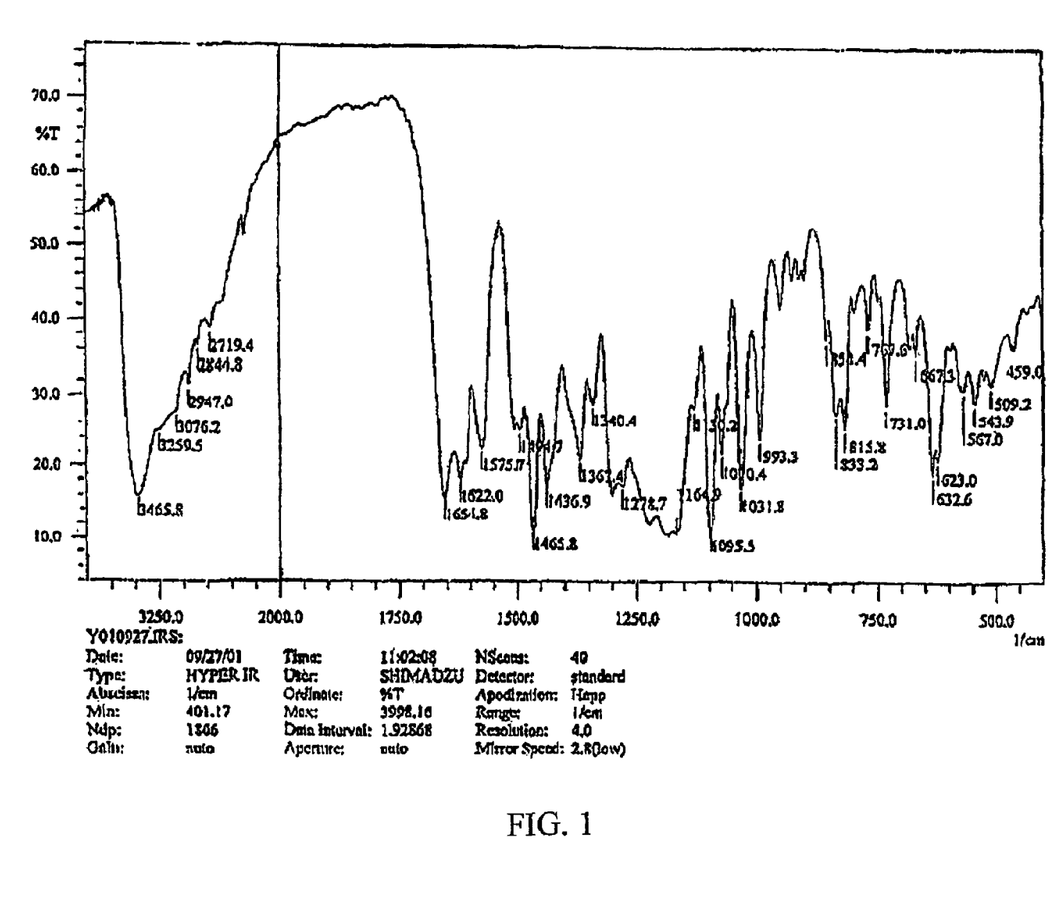
FIG. 1 is a IR spectrum of the tectorigenin sodium sulfonate compound as shown in formula (III)
Figure 2:
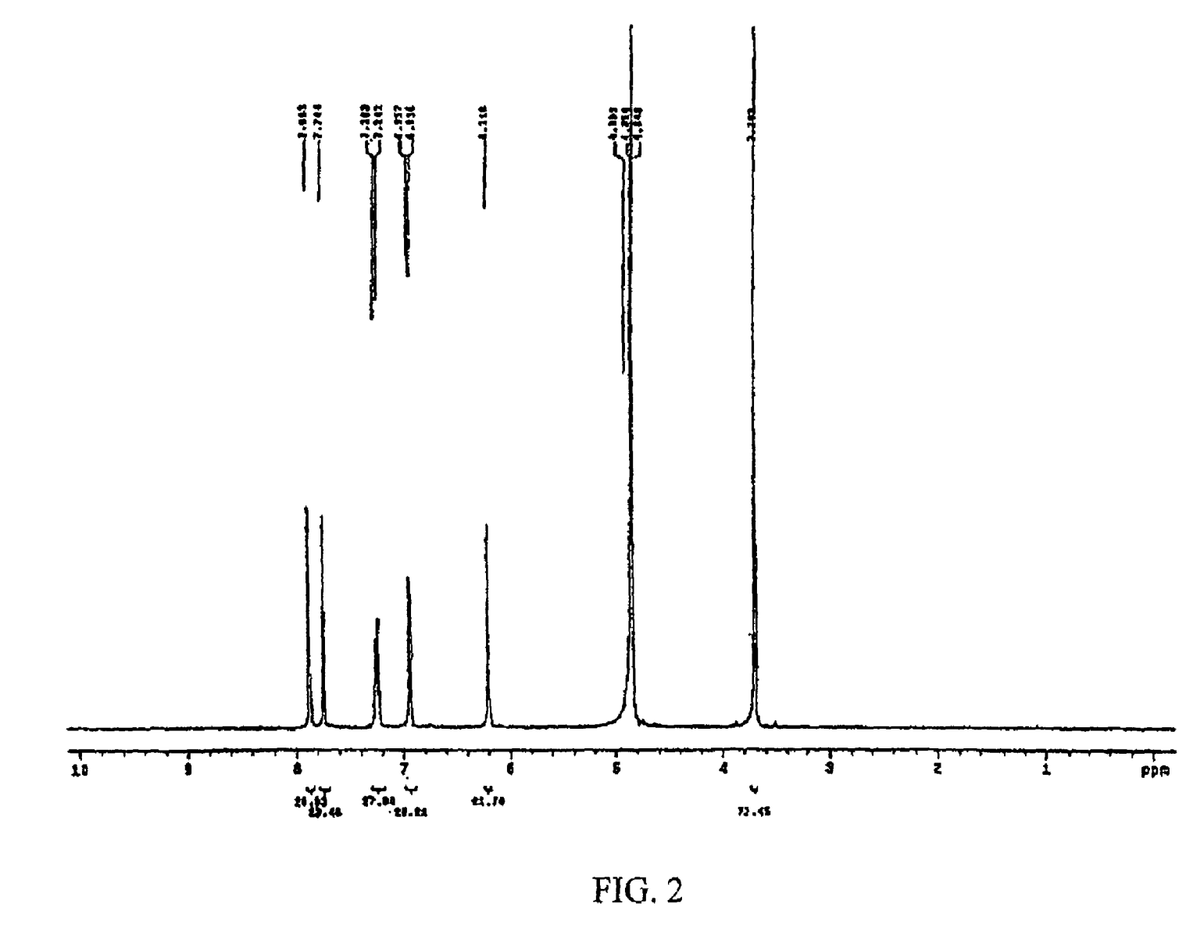
FIG. 2 is a 1HNMR spectrum of the tectorigenin sodium sulfonate compound as shown in formula (III)

120 g tectorigenin as shown in formula (II) and 480 ml concentrated sulfuric acid are mixed and agitated until they are dissolved completely, they are kept at a standstill and react for 1.5 hours, then they are poured slowly into 5000 ml saturated sodium chloride and agitated while they are added, a quantity of white sediment is released and filtered. 3000 ml water is added into the sediment, they are heated in water bath until the sediment is completely dissolved, it is filtered while it is hot, a yellow flat crystal is obtained by crystal release and filtering. 1000 ml water is added into the crystal, the mixture is heated in water bath until the crystal is completely dissolved, it is filtered while it is hot, the crystal is released and filtered. The sediment is dried at reduced pressure at 60° C., 150 g refined sodium sulfonate product of the tectorigenin as shown in formula (IV) is achieved, it is faint yellow thin and slender crystal and its content >98%.

Spectrometric data of the achieved sodium sulfonate product of the tectorigenin as shown in formula (IV) is as follows:

IR (KBr compressed tablet, $cm^{-1}$): 3465(s), 1654(s), 1622(s), 1575(s), 1494, 1465(s), 1436, 1367, 1340, 1278, 1165(s), 1095(s), 1070, 1031(s), 993, 833, 815, 767, 731, 667, 632, 567, 543, 509, 459;

1HNMR ($D_2O$ is solvent, TMS internal standard, δ Hppm): 7.88 (s, 1H), 7.74 (s, 1H), 7.25 (d, 1H), 6.94 (d, 1H), 6.21 (s, 1H), 3.70 (s, 3H).

EXAMPLE 2

Preparation of Compound (V)

300 g (1.0 mmol) the tectorigenin isoflavone (I) (it is shortly called hereinafter the raw material) is mixed with 5 ml concentrated sulfuric acid, the mixture is heated and agitated for three hours at 60° C., cooled down and poured into 20 ml saturated sodium chloride solution. It is kept at a standstill and filtered, the obtained solid matter is recrystallized by use of 5% sodium chloride solution, 283 mg intermediate product with faint yellow crystal is achieved and its yield is 70%.

150 mg (0.294 mmol) of the above-mentioned intermediate product is suspended in 5 ml ethanol, a pretreated strong-acid cation resin is added excessively into it, the mixture is agitated for an hour at room temperature and the suspended solid matter is completely dissolved. The mixture is filtered and the resin is washed by acetone. 55 mg thiethanolamine is added into the filtrate, the solvent is evaporated out at reduced pressure, a powdery solid matter compound (V) is achieved by adding dichloromethane and acetone, its yield is 90% and melting point: 155~159° C. Its solubility in water is more than 50 mg/ml.

1H NMR (400 MHz, $D_2O$) δ: 7.92 (s, 1H), 7.78 (s, 1H), 7.32 (d, J=7.2 Hz, 1H), 7.00 (d, J=8.0 Hz, 1H), 6.27 (s, 1H), 3.96 (t, J=5.2 Hz, 6H), 3.74 (s, 3H), 3.47 (t, J=5.2Hz, 6H).

13C NMR (100 MHz, $D_2O$) δ: 182.4, 159.0, 156.5, 155.7, 155.0, 154.1, 135.8, 133.2, 130.3, 124.1, 123.2, 119.6, 106.9, 96.9, 62.8, 57.8, 57.5.

IR $cm^{-1}$(KBr): 3356 (OH, NH), 3151, 1655 (C=O), 1612, 144, 1291, 1168, 1090.

ESI MS: 379.1 [M–NH(CH$_2$CH$_2$OH)$_3$]$^-$.

Elementary analysis: C$_{22}$H$_{27}$NO$_{12}$S (%): C, 49.84, H, 5.22, N, 2.71; Calculated value: C, 49.90, H, 5.14, N, 2.65.

EXAMPLE 3

Preparation of Compound (VI)

300 mg (1.0 mmol) of the tectorigenin isoflavone (I) (it is shortly called hereinafter the raw material) is dissolved in 5 ml ethanol, the ethanol solution (3 ml) mixed with 210 mg (68%) nitric acid and 500 mg concentrated sulfuric acid is added dropwise into it while it is cooled down in ice-water bath and the mixture is then agitated for 24 hours. 170 mg nitrified product is achieved after filtering and its yield is 49%.

Melting point: >200° C.

ESI MS: 346.1 (M+1)$^+$; 344.1 (M–1)$^-$.

150 mg of the above-mentioned nitro compound is dissolved in 4 ml methanol, 30 mg 10% Pd/C is added into it and the compound is completely hydrogenated at atmospheric pressure (5 h). The product is dissolved in 5 ml ethyl acetate after filtering and methanol removal at reduced pressure and the ethyl acetate HCl solution is added into it up to acidity (pH=2-3). The hydrochloride product as shown in formula (VI) is achieved after filtering, its yield is 80% and melting point: >250° C. Its solubility in water is more than 1 mg/ml.

The relevant structure test data:

1H NMR (400 MHz, DMSO) δ: 12.94 (s, 1H), 10.78 (br.s, 1H), 10.58 (br.s, 1H), 8.34 (s, 1H), 7.48 (s, 1H), 7.25 (d, J=8.4 Hz, 1H), 7.03 (d, J=8.4 Hz, 1H), 6.55 (s, 1H), 3.76 (s, 3H).

13C NMR (100 MHz, DMSO) δ: 180.5, 157.9, 154.7, 153.4, 152.9, 150.4, 131.7, 128.0, 123.6, 122.0, 121.6, 121.2, 116.0, 105.0, 94.2, 60.2.

IR cm$^-$(KBr): 3421 (OH, NH), 3079, 1645 (C=O), 1619, 1518, 1474, 1284.

ESI MS: 316.1 (M+1)$^+$; 314.1 (M–1)$^-$.

Elementary analysis: C$_{16}$H$_{14}$ClNO$_6$ (%): C, 54.35, H, 4.15, N, 4.35; Calculated value: C, 54.63, H, 4.01, N, 3.98.

EXAMPLE 4

Preparation of Compound (VII)

300 mg (1 mmol) raw material, 135 (0.1 mmol) mg ethyl clioroacetate, 8 mg butanone and a little 5% (by volume) DMF are mixed, 207.3 mg (1.5 mmol) waterless K$_2$CO$_3$ and a catalytic quantity (about 5 mol %) of NaI are added into them and the mixture is recycled while agitated. It is cooled down to room temperature, the insoluble matter is filtered out, the filtrate is concentrated at reduced pressure, the residue is dissolved in an appropriate quantity of water, extracted by ethyl acetate, water-washed twice and dried, the solvent is concentrated at reduced pressure and separated by a rapid chromatographic column, a faint yellow solid intermediate product is achieved and its yield is 39.3%. Its melting point is 164~167° C.

1H NMR (400 MHz, CDCl$_3$) δ: 12.85 (s, 1H), 7.89 (s, 1H), 7.36 (d, J=8.4 Hz, 2H), 6.86 (d, J=8.4 Hz, 2H), 6.35 (s, 1H), 5.51 (s, 1H), 4.81 (s, 2H), 4.31 (q, J=7.2 Hz, 2H), 3.98 s, 3H), 1.33 (t, J=7.2 Hz, 3H).

ESI MS: 387.2 (M+1)$^+$.

125 mg (0.32 mmol) of the intermediate product is dissolved in 4 ml methanol, 64.8 mg (1.6 mmol) NaOH is formulated into aqueous solution (1 mmol/ml), and it is added dropwise into the above-mentioned methanol solution while it is agitated, reacts for 24 hours at normal atmospheric temperature up to complete hydrolysis, the solution pH value is regulated to pH3~4 by diluted hydrochloric acid, the methanol is evaporated out at reduced pressure, the generated white flocculent sediment is dissolved in ethyl acetate, water-washed, dried, concentrated and reacts with NaHCO$_3$ to form a sodium salt as shown in formula (VII), its yield is 80% and melting point: >250° C. Its solubility in water is more than 2 mg/ml.

1H NMR (400 MHz, DMSO) δ: 9.24 (s, 1H), 10.58 (br.s, 1H), 8.32 (s, 1H), 7.24 (d, J=8.4 Hz, 2H), 6.72 (d, J=8.4 Hz, 2H), 6.47 (s, 1H), 4.38 (s, 2H), 3.78 (s, 3H).

13C NMR (50 MHz, DMSO) δ: 180.7, 170.3, 158.9, 158.2, 154.2, 152.9, 152.6, 132.2, 130.0, 122.3, 120.7, 115.4, 105.5, 92.2, 68.5, 60.1.

IR cm$^{-1}$(KBr): 3420 (OH), 1655(C=O), 1614, 1422, 1290, 1176.

ESI MS: 359.1 (M–Na+2)$^+$, 357.0 (M–Na)$^-$.

Elementary analysis: C$_{18}$H$_{13}$NaO$_8$ (%): C, 56.82, H, 3.32; Calculated value: C, 56.85, H, 3.45.

EXAMPLE 5

Preparation of Compound (VIII)

14.5 ml (0.12 mmol) dichlorosulfoxide is put into a dry round-bottomed flask, β-dimethylaminoethanol is added dropwise by use of a dropping funnel while it is cooled down in ice-water bath and the solution is fiercely agitated. A brown stickum is obtained after adding, agitated for an hour at 35~50° C., recrystallized by adding 50 ml waterless ethanol and a β-dimethylaminochloride hydrochloride intermediate product is achieved. It is washed by an appropriate quantity of waterless ethanol and ethyl ether and stored under hermetically sealed condition.

150 mg (0.5 mmol) raw material is dissolved in 15 ml butanone, 3214 mg (1.55 mmol) waterless K$_2$CO, 0.5 ml DMF and a catalytic quantity (about 5 mol %) of NaCl are added into them, the mixture is heated up to recycling, 115.3 mg (0.8 mmol) of the above-mentioned intermediate product is added in batches (every half an hour in five batches) in the mixture, the latter is recycled at about 80° C. for 48 hours and cooled down, the insoluble matter is filtered out, the filtrate is concentrated in a rotary evaporator at reduced pressure until it is dried and a stickum is achieved. It is extracted by ethyl acetate, water-washed, dried and concentrated after dilution by an appropriated quantity (ten times by weight) of water, a yellow solid product compound (VIII) is achieved and its yield is 46.5%. The hydrochloride is made by use of a conventional method. Its t melting point 190° C. (softened) and 235° C. (decomposed). Its solubility in water is more than 2 mg/ml.

1H NMR (400 MHz, DMSO) δ: 12.98 (s, 1H), 10.57 (br.s, 1H), 9.69 (s, 1H), 8.49 (s, 1H), 7.41 (d, J=8.4 Hz, 2H), 6.94 (s, 1H), 6.84 (d, J=8.1 Hz, 2H), 4.54 (t, J=5.2 Hz, 2H), 3.78 (s, 3H), 3.58 (t, J=4.8 Hz, 2H), 2.89 (s, 6H).

13C NMR (50 m MHz, DMSO) δ : 180.9, 157.8, 157.2, 157.0, 154.8, 153.0, 132.2, 130.3, 122.4, 121.1, 115.4, 106.5, 92.4, 64.4, 60.5, 55.2, 43.2.

IR cm$^{-1}$(KBr): 3418 (OH, NH), 1656 (C=O), 1614, 1515, 1460, 1272.

ESI MS: 372.1 (M+1)$^+$.

Elementary analysis: C$_{20}$H$_{22}$ClNO$_6$ (%): C, 58.85, H, 5.78, N, 3.64; Calculated value: C, 58.90, H, 5.44, N, 3.43.

EXAMPLE 6

Preparation of Compound (IX)

300 mg (1.0 mmol) raw material, 81 mg (1.0 mmol) formaldehyde solution with its content of 37% (by weight), piperidine (two equivalents) and 5 ml dioxane are mixed and then recycled for three hours. A faint yellow solid product (IX) is obtained after cooling down and filtering. The corresponding hydrochloride is achieved by adding an appropriate quantity of concentrated hydrochloric acid into it and its yield is 90%. It melting point: 245° C. (decomposed). Solubility in water is less than 1 mg/ml.

1H NMR (400 MHz, DMSO) δ: 13.43 (s, 1H), 11.26 (s, 1H), 10.03 (br.s, 1H), 9.74 (s, 1H), 8.42 (s, 1H), 7.38 (d, J=8.4 Hz, 2H), 6.86 (d, J=8.4 Hz, 2H), 4.30 (s, 2H), 3.82 (s, 3H), 3.45-3.38 (m, 2H), 2.97 (m, 2H), 1.78-1.63 (m, 4H), 1.38-1.36 (m, 1H), 1.07-1.04 (m, 1H).

13C NMR (50 MHz, DMSO) δ : 181.0, 157.9, 157.1, 154.3, 152.4, 131.1, 130.2, 122.1, 120.9, 115.4, 105.0, 95.5, 80.5, 56.2, 52.1, 48.2, 22.4, 21.2, 18.8.

IR $cm^{-1}$(KBr): 3197 (OH, NH), 2954, 1652 (C=O), 1585, 1515, 1458, 1374, 1226.

ESI MS: 398.0 $(M+1)^+$; 396.2 $(M-1)^-$.

Elementary analysis: $C_{22}H_{24}ClNO_6$ (%): C, 60.50, H, 5.74, N, 3.54; Calculated value: C, 60.90, H, 5.58, N, 3.23.

EXAMPLE 7

Preparation of Compound (X)

150 mg (0.5 mmol) raw material, 40.5 mg (0.5 mmol) formaldehyde solution with its content of 37% (by weight), 61.2 mg (0.75 mmol) dimethylamine hydrochloride and 2 ml dioxane are mixed and recycled at 70~80° C. for 10 hours, the compound (X) is achieved after cooling, filtering and collecting the insoluble matter. The product hydrochloride is achieved after its recrystallizing by ethanol under acid (hydrochloric acid pH=2~3) condition and its yield is 38.7%. Its melting point: 248° C. (decomposed). Its solubility in water is more than 2 mg/ml. This product's position selectivity is as the same as that of the above-mentioned compound (VII).

1H NMR (400 MHz, DMSO) δ: 13.40 (s, 1H), 11.32 (brs, 1H), 10.23 (brs, 1H), 9.74 (s, 1H), 8.40 (s, 1H), 7.38 (d, J=8.4 Hz, 2H), 6.85 (d, J=8.4 Hz, 2H), 4.34 (S, 1H), 3.81 (s, 3H), 2.77 (s, 6H).

13C NMR (100 MHz, DMSO) δ: 181.0, 157.9, 156.9, 154.3, 154.2, 152.3, 131.1, 130.2, 122.2, 120.9, 115.4, 105.0, 95.9, 60.6, 48.6, 42.3.

IR $cm^{-1}$(KBr): 3145 (OH, NH), 1656 (C=O), 1577, 1462, 1379, 1223.

ESI MS: 357.9 $(M+1)^+$; 356.2 $(M-1)^-$.

Elementary analysis: $C_{19}H_{20}ClNO_6$ (%): C, 57.99, H, 5.11, N, 3.85; Calculated value: C, 57.95, H, 5.12, N, 3.56.

EXAMPLE 8

Preparation of Various Dosage-form Medicines

1. Injection Preparation

The glucose with 2~15% weight/volume ratio of the total injection quantity is added as a solubilizer, so that its solubility in water is greatly increased because hydrogen bond is formed by association of the polyhydroxy in glucose with isoflavone group.

The tectorigenin sodium sulfonate is taken as an example, its water-solubility is only 20 mg/ml (2%) at room temperature and could not reach the medication concentration, its water-solubility could be increased to 50-60 mg/ml (5~6%) after heating to 60-100° C. and the sediment is released again after cooling down to room temperature. However, after 2-15% glucose is added into the injection it can be kept clarified at room temperature and low temperature (0° C.-5° C.), can also be diluted arbitrarily by water or sugar saline water and does not become turbid. Therefore, it not only can be used for intramuscular injection, but also for intravenous injection when it is added into sugar and/or saline water. This just indicates that the injection preparation medicine stability can also be increased greatly at the same time when the tectorigenin sodium sulfonate solubility in water is increased by glucose.

100 g tectorigenin sodium sulfonate and 150 g glucose for injection are dissolved in 1500 ml water for injection, the water for injection is added up to a 2000 ml volume after they are completely dissolved, the filtrate is packed in ampoule bottles and sterilized in a conventional way after filtering by use of a G4 sintered glass funnel. The obtained injection is a faint yellow clarified liquid.

100 g of the compound as shown in formula (V) and 100 g glucose for injection are dissolved in 1500 ml water for injection, the water for injection is added up to a 2000 ml volume after they are completely dissolved, the filtrate is packed in ampoule bottles and sterilized in a conventional way after filtering by use of a G4 sintered glass funnel. The obtained injection is a faint yellow clarified liquid.

100 g tectorigenin sodium sulfonate and 80 g glucose for injection are dissolved in 1500 ml water for injection, the water for injection is added up to a 2000 ml volume after they are completely dissolved, the filtrate is packed in ampoule bottles and sterilized in a conventional way after filtering by use of a G4 sintered glass funnel. The obtained injection is a faint yellow clarified liquid, then lyophilized in a lyophilizer for 15-28 hours and a yellow loose lyophilized powder for injection is thus achieved.

2. Preparation of the Oral Preparations

The oral preparations include: the tablet, powder, granule, capsule, pill, dropping-pill, mini-pill and various solutions etc.

The powder is a basis of various dosage forms as a solid oral preparation, since all derivatives synthesized by us are the faint yellow and yellow solids and achieved by drying, finely grinding (it means that all the fine powder can pass through a sieve #5 and contain ≧95% powder which can pass through a sieve #6). The powder is obtained after sieving, adding an appropriate quantity of talcum powder auxiliary material for increasing its fluidity and packing.

Granule preparation: the medicine and auxiliary materials are fully mixed after grinding and then granulated after adding an appropriate adhesive into it, dried, granule-sorted and packed.

Capsule preparation: the capsules are classified as soft and hard ones. The hard capsule is made by the medicinal powder or granule capsulation and the soft capsule is made by the medicinal solution charging in a spherical or soft capsule material. An appropriate material—dry gelatin is evenly mixed with glycerine and water in a 1:0.4 glycerine-water ratio to be used as the soft capsule wall, the solution medicine pH value is regulated to 4.5-7.5 and the soft capsule can also be made from solid medicinal powder which should pass through the mesh #80 by dropping or compressing process. Besides, the enteric capsule can also be made.

In addition, various auxiliary materials such as ethylene-vinyl acetate copolymer (EVA) and polypropylene etc. can be selected and used to make skeletons for the slow-released and control-released preparations according to the routine preparation procedure. For example, the tectorigenin derivative medicine can become a product released as required by its mini-capsulation and then charging it in an empty common capsule.

Dripping-pill or mini-pill: the dropping-pill's advantages are its quick effect, high bioavailability, small side effect, convenient drug-taking and transportation of the solid pill made from liquid medicine, drug stability increase, simple productive equipment, easy operation, small difference in weight, low cost, no dust and many types of dropping-pills can be made for oral mediation, external use, slow release, controlled release or local curing etc.

Medicinal solution is evenly mixed with the medicinal substrate (the substrate is heated) such as polyethylene glycol and stearic acid, the mixture is put in a dropping-pill machine for heat preservation, then dropped to a receptacle in an appropriate condensing agent, dried and sorted after washing out the condensing agent and packed after quality control.

Tablet

The tablets include the ordinary compressed, masticatory, effervescent, multiple compressed, slow-released, control-released, coated (sugar coated, film-coated and enteric-coated), dispersing, buccal and sublingual etc. tablets.

50 g tectorigenin derivative and 950 g starch and powdered sugar are evenly mixed after grinding and sieving of the above raw and auxiliary materials, an appropriate quantity of adhesive is added into them to form a soft material, they are sieved, granulated, dried, sorted, fully mixed after adding a disintegrant and lubricant into them, compressed, coated, quality controlled and then packed.

Slow-released and Control-released Tablets 50 g tectorigenin derivative is evenly mixed with polyethylene or polypropylene skeleton, compressed and made into 1000 slow-released tablets according to the ordinary preparation process. The drug is slowly released and the skeleton is excreted with dejecture after drug releasing.

3. Preparation of the Preparations for External Use

They include: the lotion, eye drops, spray, eye ointment, gel, suppository, liniment, ointment, nose drops, ear drops, film agent and transdermal sticker etc.

Eye ointment: as a raw material the derivative is ground into extremely fine powder (it means that all powder can pass through a sieve #7 and it contains more than 95% powder which can pass through a sieve #8) and made into the gel for eye use or the eye ointment after adding an appropriate substrate.

The raw and auxiliary materials of the powder for external use are ground into very fine powder (it means that all powder can pass through a sieve #6 and it contains more than 95% powder which can pass through a sieve #7). The powder for external application can be generally used to kill virus or prevent from virus infection.

Eye drops: 20 g tectorigenin derivative as a raw material is made into the eye drops, it's pH value is regulated to 5.9~8.0 by adding a phosphate buffer solution pH value regulator in it, its osmotic pressure is regulated to that equivalent to 0.6-1.5% sodium chloride osmotic pressure by adding an appropriate quantity of glucose osmotic pressure regulator in it, the solution is filtered after adding a small quantity of viscosity regulator (polyethylene glycol) and 980 g water in it, the filtrate can be packed in bottles under aseptic condition after sterilization.

Preparation method of the spray, nose drops and ear drops are similar, but their osmotic pressure and pH value requirements are not very strict.

Ointment and Liniment 40 g tectorigenin derivative is ground into very fine powder and dissolved in 960 g water-soluble substrate polyoxyethylene glycol 600 and 2000 (4:6 ratio), the mixture is packed after heating, even mixing and quality control and a semisolid preparation with a certain thickness for external use can be achieved.

Gel 40 g tectorigenin derivative is ground and dissolved in water, a water-soluble substrate Carbopol is made into hydrogel substrate, the latter is mixed with the drug, water is added up to 1000 ml and a transparent or semitransparent gel can be achieved after quality control and packing.

Suppository 40 g tectorigenin derivative is ground into very fine powder and dissolved in 960 g water-soluble substrate polyoxyethylene glycol 600 and 18000 (4:6 ratio), the mixture is poured into a mould coated with liquid paraffin after heating and even mixing, cooled down, shaped, quality controlled and packed and a solid preparation for external use with the melting time limit conforming to its stipulations can be achieved.

Film Coating Agent

A film coating preparation for external use can be achieved by dissolving both the tectorigenin derivative and high-molecular filming material polyethylene formaldehyde and acetaldehyde condensates (ratio 4:96) in ethanol.

Transdermal Sticker 60 g tectorigenin derivative is firstly finely ground and dissolved in water, the water-soluble polymers PVA or PVP are then mixed with medicinal aqueous solution to form a gel pool after even mixing with water, the latter is quality-controlled and dosed, a viscose layer, can be obtained by coating the pressure-sensitive glue (acrylics acid) on backing material (polypropylene) at the same time, the layer is divided into an area larger than medicinal pool and is then combined with the gel pool, a layer of anti-sticking material (polyethylene high polymer) is applied on its surface and the transdermal sticker is formed.

EXAMPLE 9

Acute Toxicity Test and Antiviral Effect Test of Tectorigenin Sodium Sulfonate

The following tests are carried out by taking the sodium sulfonate injection of tectorigenin (50 mg/ml) as shown in the above-mentioned formula (IV) as an experimental sample:

1. Acute Toxicity Test

18~20 g weighted male and female mice (half and half) are taken as the experimental animals and they are dosed by intramuscular, intravenous and intraperitoneal injection respectively. 0.2 ml/10 g (500 mg/kg) dosage is injected in their rear leg muscle on both sides. respectively for intramuscular injection (im); they are dosed in caudal vein in all groups for intravenous injection (iv) and the dosage is 841.5 mg/kg, 781.25 mg/kg, 725.25 mg/kg, 673.25 mg/kg and 580.2 mg/kg respectively; the dosage for intraperitoneal injection (ip) is 0.4 mg/10 g (i.e. equivalent to 1000 mg/kg). The experimental animals toxicity reaction and death after dosing in all groups are observed respectively once a day for 14 days. Once an animal death is found out it is dissected immediately. The half lethal dose is measured by use of the median effective dose probability unit method (the weighted linear regression method). Experimental result: ①Abnormality was not found out in respect of the reactions such as spiritual condition, pilous condition, diet, drinking, growth and development of the experimental animals dosed by intramuscular injection and none of 20 mice died in 14 days after injection, so that the maximum tolerance dose of the mice dosed once by intramuscular injection is 500 mg/kg and their half lethal dose ought to be over 500 mg/kg. ②The half lethal dose of the experimental animals dosed by intravenous injection LD50=725.81 mg/kg and their 95% confidence limit is 669.92 mg/kg~785.53 mg/kg; the half lethal dose measured by sequential method in the pilot test product is LD50=868.2 mg/kg and LD50 95% confidence limit is 798.2~944.4 mg/kg. ③ None of the experimental animals dosed by intraperitoneal injection died in 14 days and the maximum tolerance dose of the mice dosed once by intraperitoneal injection is 1000 mg/kg.

Result of the acute toxicity test conducted by three dosage ways indicates that the above-mentioned antiviral injection used as a test sample has a low toxicity, LD50 was not measured out in the case of dosing by im and ip, the maximum tolerance dose is 500 mg/kg and 1000 mg/kg respectively; LD50 is 725.81 mg/kg and 868.2 mg/kg in the case of dosing by iv.

2. In Vitro Antiviral Test

The test drug is the above-mentioned injection sample in this invention, the control drug is Potassium Sodium Dehydroandroandrographolide Succinate for Injection (Trade name: Chuanhuning for injection, 40 mg/ml(lot No.: 000501, produced by Chengdu Pharmaceutical Factory No. 3, chemical structure:

and the blank control is Hanks liquor (provided by the virus laboratory, laboratory section, Sichuan Provincial People's Hospital).

Experimental strain is: Hep-2 and HL16C cells (they are all provided by the cell engineering research section, Shantou Huaying Bioengineering Application and Research Institute). The virus strain is a mixed cell strain of the adenovirus ADV3 type and ADV7 type, respiratory syncytial virus (RSV), influenza virus (Flu•V) type A1 and type A3 and the Coxsackie virus group B (CoxBV) (they are provided by the Capital Research Institute of Pediatrics, the virus research institute of China's Preventive Medical Science Research Institute and Sichuan Provincial Sanitary and Anti-epidemic Station respectively) and TCID50 is measured before test.

Test Method (1) Cell Toxicity Test

The test sample injection and Chuanhuning for injection are diluted respectively by Hanks liquor from 10 mg/ml according to the law of multiple proportions, two solutions after dilution are 10 mg/ml, 5 mg/ml, 2.5 mg/ml and 1.25 mg/ml. The above two drugs with four different concentration are vaccinated respectively in Hep-2 and Z-HL16C cells, the cell control is synchronously set up, 2% calf blood serum Eagles maintenance media is added into them; they are kept at 37° C. in a thermostat and the above-mentioned cell toxic reaction is observed day by day. The cell toxicity test result is shown in table 2.

TABLE 2

The cell toxicity test result

| Drug | Virus | Concentration (mg/ml) | | | | Virus control | Control cell |
|---|---|---|---|---|---|---|---|
| | | 10 | 5 | 2.5 | 1.25 | | |
| Test sample | Hep-2 | — | — | — | — | — | — |
| | Z-HL16C | — | — | — | — | — | — |
| Chuanhuning | Hep-2 | — | — | — | — | — | — |
| | Z-HL16C | — | — | — | — | — | — |
| Blank control (Hanks liquor) | Hep-2 | — | — | — | — | — | — |
| | Z-HL16C | — | — | — | — | — | — |

(Note: "—" means that no any toxic reaction occurred in the cells)

The result in table 2 indicates that the test sample solution, control drug Chuanhuning and blank control (Hanks liquor) have no any toxic reaction to Hep-2 and Z-HL16C cells.

(2) Antiviral Test

100TCID50 ADV3, ADV7, Flu•V type A1 & A3, CoxBV and RSV viruses are vaccinated in Hep-2 and Z-HL16C cells respectively (Flu•V type A1 & A3 are vaccinated in Z-HL16C cell), the virus solution is washed off after absorption in 30 minutes and the test sample and Chuanhuning non-toxic limit solution are added into it respectively (i.e. 10 mg/ml, 5 mg/ml, 2.5 mg/ml and 1.25 mg/ml), the virus control, cell control and blank control (Hanks liquor) are set up at the same time synchronously with the above drugs. The cell maintenance medium is 2% calf blood serum Eagles medium, it is kept at 37° C. in an incubator, the Hep-2 and Z-HL16C cells pathologic change is observed and the cell pathologic change in all groups is recorded day by day. As for RSV resisting test, after the viruses and non-toxic limit drug are vaccinated the solution is placed horizontally at 37° C. in incubator for 24 hours, then removed to a rotary incubator (12 revs/min) at 35° C. and the cell pathologic change is observed day by day. When pH value is declined in culture tubes the solution should be changed immediately. Once 2+~3+pathologic change occurs in the virus control groups while the cells are normal and grow well in the cell control groups in the test, it should be terminated. The test result is shown in table 3.

The result in table 3 demonstrates that 10 mg/ml test sample injection solution in the invention has an inhibiting effect on ADV3, ADV7, CoxBV, Flu•V type A1 and RSV cytopathogenesis and a partially inhibiting effect on Flu•V type A3.5 mg/ml solution: has an inhibiting effect on Flu•V type A1 and RSV cytopathogenesis and a partially inhibiting effect on ADV3 and CoxBV. 2.5 mg/ml solution has an inhibiting effect on Flu•V A1. 10 mg/ml Chuanghuning solution has an inhibiting effect on ADV3 & 7, CoxBV, Flu•V A1 and RSV cytopathogenesis. The solution with other concentration and the blank control in all tubes can not inhibit the cell pathologic change.

TABLE 3

Antiviral test report

| Drug | Virus | Concentration (mg/ml) | | | | Virus control | Control cell |
|---|---|---|---|---|---|---|---|
| | | 10 | 5 | 2.5 | 1.25 | | |
| Test sample | AdV$_3$ | — | 1+ | 2+ | 3+ | 3+ | — |
| | AdV$_7$ | — | 2+ | 3+ | 3+ | 3+ | — |
| | CoxBV | — | 1+ | 2+ | 3+ | 3+ | — |

TABLE 3-continued

Antiviral test report

| Drug | Virus | Concentration (mg/ml) | | | | Virus control | Control cell |
|---|---|---|---|---|---|---|---|
| | | 10 | 5 | 2.5 | 1.25 | | |
| | Flu·$V_{A1}$ | — | — | — | 2+ | 3+ | — |
| | Flu·$V_{A3}$ | 1+ | 2+ | 2+ | 3+ | 3+ | — |
| | RSV | — | — | 2+ | 3+ | 3+ | — |
| Chuanhuning | $AdV_3$ | — | 2+ | 2+ | 3+ | 3+ | — |
| | $AdV_7$ | — | 2+ | 2+ | 3+ | 3+ | — |
| | CoxBV | — | 2+ | 2+ | 3+ | 3+ | — |
| | Flu·$V_{A1}$ | — | 2+ | 2+ | 3+ | 3+ | — |
| | Flu·$V_{A3}$ | 2+ | 2+ | 2+ | 3+ | 3+ | — |
| | RSV | — | 2+ | 3+ | 3+ | 3+ | — |
| Blank control | $AdV_3$ | 3+ | 3+ | 3+ | 3+ | 3+ | — |
| (Hanks liquor) | $AdV_7$ | 3+ | 3+ | 3+ | 3+ | 3+ | — |
| | CoxBV | 3+ | 3+ | 3+ | 3+ | 3+ | — |
| | Flu·$V_{A1}$ | 3+ | 3+ | 3+ | 3+ | 3+ | — |
| | Flu·$V_{A3}$ | 3+ | 3+ | 3+ | 3+ | 3+ | — |
| | RSV | 3+ | 3+ | 3+ | 3+ | 3+ | — |

(Note: "—" means that no pathologic change occurred in the cells. 1+-3+ means the cell pathologic change degree.)

The above mentioned test result demonstrates that the test sample injection with a 10 mg/ml concentration has an inhibiting effect on ADV3, ADV7, CoxBV, Flu•V type A1 & A3 and RSV to different extent in the case of 100TCID50 virus infection and has an excellent effect on Flu•V type A1 and RSV. 10 mg/ml Chuanhuning (control drug) solution has an inhibiting effect on ADV3, ADV7, CoxBV, Flu•V type A1 & A3 and RSV. The test result points out that the inhibiting effect of the test sample injection in the invention on Flu•V type A1 and RSV can be better than that of Chuanhuning used for injection at present.

EXAMPLE 10

Antivirotic Effect Test

The following pharmaceutical effect tests are carried out by taking the typical tectorigenin derivative in above-mentioned examples as the test sample.

1. Antiviral Test

The test drugs are the injection sample, oral capsule, granule, tablet, solution as well as the eye drops, liniment, cream, lotion and ear drops for external use made from the derivative in the invention. The control drug is Potassium Sodium Dehydroandroandrographolide Succinate for Injection (Trade name: Chuanhuning for injection, 40 mg/ml, made by Chengdu Pharmaceutical Factory No. 3). The virazole blank control is Hanks liquor (provided by the virus laboratory, laboratory section, Sichuan Provincial People's Hospital).

Experimental cell strains are: Hep-2 and Z-HL16C cells (all provided by the cell engineering section, Military Medical University No. 4). The virus strain is: a complete mixed strain of adenovirus ADV3, ADV7, respiratory syncytial virus (RSV), influenza virus (Flu•V) A1 & A3 and Coxsackie virus group B (CoxBV) (provided by the virus research institute of China's Preventive Medical Science Research Institute and Sichuan Provincial Sanitary and Anti-epidemic Station respectively) and TCID50 is measured before test respectively.

Test Method (1) Cell Toxicity Test

The test sample injection, oral capsule, granule, tablet, pill, eye drop, eye ointment and other preparations for external use are dissolved and formulated with a concentration as required and Chuanhuning for injection is diluted by Hanks liquor from 10 mg/ml according to the law of multiple proportions and its solution after dilution is: 10 mg/ml, 5 mg/ml, 2.5 mg/ml and 1.25 mg/ml. The above two drugs with four different concentration are vaccinated in Hep-2 and Z-HL16C cells, the cell control is set up synchronously, 2% calf blood serum Eagles maintenance media is added enough, they are kept in thermostat at 37° C. and the above cell toxicity reaction is observed day by day. The cell toxicity test result is shown in table 4.

TABLE 4

Cell toxicity test result

| Drug | Cell | Concentration (mg/ml) | | | | Control cell |
|---|---|---|---|---|---|---|
| | | 8 | 5 | 2.5 | 1.25 | |
| Compound (V) | Hep-2 | — | — | — | — | — |
| | Z-$HL_{16}$C | — | — | — | — | — |
| Compound (VI) | Hep-2 | — | — | — | — | — |
| | Z-$HL_{16}$C | — | — | — | — | — |
| Compound (VII) | Hep-2 | — | — | — | — | — |
| | Z-$HL_{16}$C | — | — | — | — | — |
| Compound (VIII) | Hep-2 | — | — | — | — | — |
| | Z-$HL_{16}$C | — | — | — | — | — |
| Compound (IX) | Hep-2 | — | — | — | — | — |
| | Z-$HL_{16}$C | — | — | — | — | — |
| Compound (X) | Hep-2 | — | — | — | — | — |
| | Z-$HL_{16}$C | — | — | — | — | — |
| Blank control (Hanks liquor) | Hep-2 | — | — | — | — | — |
| | Z-$HL_{16}$C | — | — | — | — | — |

(Note: "—" means that no any toxic reaction occurred in the cells)

The result in table 4 demonstrates that the test sample solution, control drug Chuanhuning and blank control (Hanks liquor) have no any toxic reaction to Hep-2 and Z-HL16C cells in all dosage groups.

(2) Antiviral Test

100TCID50, ADV3, ADV7, Flu•V type A1 & A3, CoxBV and RSV viruses are vaccinated in Hep-2 and Z-HL16C cells respectively (Flu•V type A1 & A3 are vaccinated in Z-HL16C cell), the virus solution is washed off after adsorption in 30 minutes and the test sample and Chuanhuning non-toxic limit solution are added into it respectively (i.e. 8 mg/ml, 5 mg/ml, 2.5 mg/ml and 1.25 mg/ml), the virus control, cell control and blank control (Hanks liquor) are set up at the same time synchronously with the above drugs. The cell maintenance media is 2% calf blood serum Eagles media, it is kept at 37° C. in an incubator, the Hep-2 and Z-HL16C cells pathologic change is observed and the cell pathologic change in all groups is recorded day by day. As for RSV resisting test, after the viruses and non-toxic limit drug are vaccinated the solution is placed horizontally at 37° C. in an incubator for 24 hours, then removed to a rotary incubator (12 revs/min) at 35° C. and the cell pathologic change is observed day by day. When pH value is declined in tubes the solution should be changed immediately. Once 2+~3+pathologic change occurs in the virus control groups while the cells are normal and grow well in the cell control groups in the test, it should be terminated. The test result is shown in table 5.

The result in table 5 demonstrates that 10 mg/ml test sample injection solution in the invention has an inhibiting effect on ADV3, ADV7, CoxBV, Flu•V type A1 and RSV cytopathogenesis and a partially inhibiting effect on Flu•V type A3.5 mg/ml solution has an inhibiting effect on Flu•V type A1 and RSV cytopathogenesis and a partially inhibiting effect on ADV3 and CoxBV. 2.5 mg/ml solution has an inhibiting effect on Flu•V type A1. 8 mg/ml Chuanghuning solution has an inhibiting effect on ADV3 & 7, CoxBV, Flu•V type A1 and RSV cytopathogenesis. The solution with other concentration and the blank control in all tubes can not inhibit the cell pathologic change.

TABLE 5

Antiviral test report

| Drug | Virus | Concentration (mg/ml) | | | | Virus control | Control cell |
|---|---|---|---|---|---|---|---|
| | | 8 | 5 | 2.5 | 1.25 | | |
| Compound (V) | $AdV_3$ | — | 1+ | 1+ | 2+ | 3+ | — |
| | $AdV_7$ | — | 1+ | 2+ | 2+ | 3+ | — |
| | CoxBV | — | 1+ | 1+ | 3+ | 3+ | — |
| | $Flu \cdot V_{A1}$ | — | — | — | 2+ | 3+ | — |
| | $Flu \cdot V_{A3}$ | — | 1+ | 2+ | 3+ | 3+ | — |
| | RSV | — | — | 2+ | 3+ | 3+ | — |
| | HSV-1 | — | — | — | 1+ | 3+ | — |
| | VZV | — | 1+ | 1+ | 1+ | 3+ | — |
| Compound (VI) | $AdV_3$ | — | 1+ | 2+ | 3+ | 3+ | — |
| | $AdV_7$ | — | 2+ | 2+ | 2+ | 3+ | — |
| | CoxBV | — | 2+ | 2+ | 2+ | 3+ | — |
| | $Flu \cdot V_{A1}$ | — | — | — | 2+ | 3+ | — |
| | $Flu \cdot V_{A3}$ | 1+ | 2+ | 3+ | 3+ | 3+ | — |
| | RSV | — | — | 2+ | 3+ | 3+ | — |
| | HSV-1 | — | 1+ | 2+ | 3+ | 3+ | — |
| | VZV | — | 2+ | 2+ | 3+ | 3+ | — |
| Compound (VII) | $AdV_3$ | — | 1+ | 1+ | 2+ | 3+ | — |
| | $AdV_7$ | — | 2+ | 3+ | 3+ | 3+ | — |
| | CoxBV | — | 1+ | 2+ | 3+ | 3+ | — |
| | $Flu \cdot V_{A1}$ | — | — | — | 2+ | 3+ | — |
| | $Flu \cdot V_{A3}$ | 1+ | 2+ | 2+ | 3+ | 3+ | — |
| | RSV | — | — | 2+ | 3+ | 3+ | — |
| | HSV-1 | — | 1+ | 1+ | 1+ | 3+ | — |
| | VZV | — | 1+ | 1+ | 2+ | 3+ | — |
| Compound (VIII) | $AdV_3$ | — | 1+ | 2+ | 3+ | 3+ | — |
| | $AdV_7$ | — | 2+ | 3+ | 3+ | 3+ | — |
| | CoxBV | — | 1+ | 2+ | 3+ | 3+ | — |
| | $Flu \cdot V_{A1}$ | — | — | — | 2+ | 3+ | — |
| | $Flu \cdot V_{A3}$ | 1+ | 2+ | 2+ | 3+ | 3+ | — |
| | RSV | — | — | 2+ | 3+ | 3+ | — |
| | HSV-1 | — | 1+ | 1+ | 2+ | 3+ | — |
| | VZV | — | — | 2+ | 2+ | 3+ | — |
| Compound (IX) | $AdV_3$ | — | 1+ | 3+ | 3+ | 3+ | — |
| | $AdV_7$ | — | 2+ | 3+ | 2+ | 3+ | — |
| | CoxBV | — | 1+ | 2+ | 3+ | 3+ | — |
| | $Flu \cdot V_{A1}$ | — | — | — | 2+ | 3+ | — |
| | $Flu \cdot V_{A3}$ | 1+ | 2+ | 2+ | 3+ | 3+ | — |
| | RSV | — | — | 2+ | 2+ | 3+ | — |
| | HSV-1 | — | — | 2+ | 2+ | 3+ | — |
| | VZV | 1+ | 2+ | 2+ | 3+ | 3+ | — |
| Compound (X) | $AdV_3$ | — | 1+ | 2+ | 3+ | 3+ | — |
| | $AdV_7$ | — | 2+ | 3+ | 3+ | 3+ | — |
| | CoxBV | — | 1+ | 3+ | 3+ | 3+ | — |
| | $Flu \cdot V_{A1}$ | — | — | — | 2+ | 3+ | — |
| | $Flu \cdot V_{A3}$ | 1+ | 2+ | 2+ | 3+ | 3+ | — |
| | RSV | — | — | 2+ | 3+ | 3+ | — |
| | HSV-1 | — | 1+ | 2+ | 3+ | 3+ | — |
| | VZV | — | — | 1+ | 2+ | 3+ | — |
| Ribavirin | $AdV_3$ | — | 1+ | 2+ | 3+ | 3+ | — |
| | $AdV_7$ | — | 2+ | 3+ | 3+ | 3+ | — |
| | CoxBV | — | 2+ | 2+ | 3+ | 3+ | — |
| | $Flu \cdot V_{A1}$ | — | 1+ | 1+ | 3+ | 3+ | — |
| | $Flu \cdot V_{A3}$ | 1+ | 3+ | 3+ | 3+ | 3+ | — |
| | RSV | — | — | 2+ | 3+ | 3+ | — |
| | HSV-1 | — | 1+ | 2+ | 3+ | 3+ | — |
| | VZV | — | 1+ | 2+ | 3+ | 3+ | — |
| Chuanhuning | $AdV_3$ | — | 2+ | 2+ | 3+ | 3+ | — |
| | $AdV_7$ | — | 2+ | 2+ | 3+ | 3+ | — |
| | CoxBV | — | 2+ | 2+ | 3+ | 3+ | — |
| | $Flu \cdot V_{A1}$ | — | 2+ | 2+ | 3+ | 3+ | — |
| | $Flu \cdot V_{A3}$ | 2+ | 2+ | 2+ | 3+ | 3+ | — |
| | RSV | — | 2+ | 3+ | 3+ | 3+ | — |
| | HSV-1 | 1+ | 2+ | 3+ | 3+ | 3+ | — |
| | VZV | 1+ | 2+ | 3+ | 3+ | 3+ | — |
| Blank control (Hanks liquor) | $AdV_3$ | 3+ | 3+ | 3+ | 3+ | 3+ | — |
| | $AdV_7$ | 3+ | 3+ | 3+ | 3+ | 3+ | — |
| | CoxBV | 3+ | 3+ | 3+ | 3+ | 3+ | — |
| | $Flu \cdot V_{A1}$ | 3+ | 3+ | 3+ | 3+ | 3+ | — |
| | $Flu \cdot V_{A3}$ | 3+ | 3+ | 3+ | 3+ | 3+ | — |
| | RSV | 3+ | 3+ | 3+ | 3+ | 3+ | — |
| | HSV-1 | 3+ | 3+ | 3+ | 3+ | 3+ | — |
| | VZV | 3+ | 3+ | 3+ | 3+ | 3+ | — |

(Note: "—" means that no cell pathologic change occurred. 1+~3+ means the cell pathologic change degree.)

The above mentioned test result demonstrates that the test sample injection in the invention with a concentration of 10 mg/ml has an inhibiting effect on adenovirus type 3 (ADV3), adenovirus type 7 (ADV7), Coxsackie virus group B (CoxBV), influenza virus type A1 (Flu•V A1) & type A3 (Flu•V A3) and respiratory syncytial virus (RSV) to different extent and has an excellent inhibiting effect on the influenza virus type A1 & A3 and the respiratory syncytial virus at the circumstance of 100TCID50 is infected. The control drug Chuanhuning solution with a concentration of 10 mg/ml has an inhibiting effect on adenovirus type 3, adenovirus type 7, Coxsackie virus group B, influenza virus type A1 & type A3 and respiratory syncytial virus (RSV). The test result points out that the inhibiting effect of the test sample in the invention on influenza virus type A1 and respiratory syncytial virus can be better than that of Chuanhuning used at present for injection and ribavirin.

(3) SARS Virus-resisting Test

The tectorigenin derivative toxicity to Vero-E6 cell and its inhibiting effect on coronavirus in Vero-E6 cell are studied by use of the virus strain BJ01 separated from a patient's lung tissue during SARS popularization in Beijing and Vero-E6 cell.

(3.1) Experimental Materials

① Tested drug: the above-mentioned tectorigenin derivatives are formulated into an injection, i.e. Dikang antiviral injection (50 mg/ml), which is provided by Sichuan Dikang Sci.-Tech Pharmaceutical Co., Ltd and its lot No.: 20030301.

② Positive control drug: Ribavirin (virazole) injection, 0.1 g/ml, provided by Shangdong Xinhua Pharmaceutical Co., Ltd, approved document No.: H19993063, lot No.: 02100020. Its clinical application: it is used to cure the viral pneumonia and bronchitis caused by respiratory tract cell virus. Its daily clinical dosage for adult is 0.5 g two times a day.

③ Cell: Vero-E6, it is stored in our cell bank (ATCC CRL-1586).

④ Virus strain: the coronavirus separated from a patient's lung tissue in February 2003 during SARS popularization in Beijing and it is named strain BJ01.

⑤ Reagent: DMEM culture medium and fetal calf blood serum, made by Gibcol1BRL Company and its lot No. is 31600-026 and 16000-36 respectively.

⑥ Instrument: a 96-porous cell culture board produced by Coming Company and a biotic inverted microscope made by Chongqing Optical Instrument Factory.

(3.2) Method and Result

① Drug Formulation Method

Tested drug: the tectorigenin derivative is a faint yellow liquid and stored at 4° C. in a refrigerator. The positive control drug is formulated into a 10 mg/ml mother liquor. It is formulated by use of cellular growth-promoting media into that with a required concentration when it is used.

② Test of the Tectorigenin Derivative Toxicity to Cell

300000~400000 Vero-E6 cells/ml are vaccinated in a 96-porous cell culture board, 0.1 ml in each pore, the board is kept at 37° C. for 18 hours in a 5% $CO_2$ incubator, the testing drug with different concentration is added into it, the drug with each concentration is added in 4 pore and 0.4 ml is in each pore, the drugless cell control group is set up at the same time, it is cultivated for 4~5 days to observe the cell pathologic change (CPE), the CPE is observed as an index in the fifth day by a biotic inverted microscope, the complete pathologic change is 4, 75% pathologic change is 3, 50% pathologic change is 2, 25% pathologic change is 1 and no pathologic change is 0. The test is repeated twice. The medium toxic concentration (TD50) and maximum nontoxic concentration (TD0) are calculated by use of REED-MUENCH method and the result is shown in table 6.

TABLE 6

The tectorigenin derivative injection toxicity to Vero-R6 cell

| Drug dilution | Drug concentration mg/ml | Pathologic change pore/cell pore | |
|---|---|---|---|
| | | tectorigenin derivative | Cell control group |
| 1:2 | 4 | 3/4 | 0/4 |
| 1:4 | 2 | 2/4 | 0/4 |
| 1:8 | 1 | 0/4 | 0/4 |
| 1:16 | 0.5 | 0/4 | 0/4 |
| 1:32 | 0.25 | 0/4 | 0/4 |

It can be seen from the calculation in table 6 that the maximum nontoxic concentration (TD0) of antiviral injection of the invention to Vero-E6 cell is 1 mg/ml and the medium toxic concentration (TD50) is 2.34 mg/ml. This means that the tectorigenin derivative of the invention has a less toxicity and better safety to Vero-E6 cell.

(4) Coronavirus-inhibiting Test of the Tectorigenin Derivative (Cell Pathologic Change Method)

The Vero-E6 cell is vaccinated in a 96-porous culture board, cultivated at 37° C. to a single-layer and the growth-promoting media is discarded. The four generation of virus solution of coronavirus BJ01 strain is diluted by DMEM maintenance media into 100 TCID50/0.1 ml, 0.1 ml of it is vaccinated in VeroE6 cell in each pore and absorbed for two hours and the virus solution is discarded. A normal cell control group, a virus control group and a positive drug control group are set up. The cell is kept at 37° C. in a 5% $CO_2$ culture incubator, its pathologic change is observed every day totally for five days, the CPE is recorded, the test is repeated twice and its result is basically identical. The median inhibiting concentration (IC50) and therapeutic index (TI) are calculated by use of REED-MUENCH method and the result is shown in table 7.

TABLE 7

Coronavirus-inhibiting effect of the tectorigenin derivative

| | | Pathologic change pore/cell pore | | | |
|---|---|---|---|---|---|
| Drug dilution | Drug concentration mg/ml | tectorigenin derivative | Virus control | Positive control drug | Normal cell control |
| 1:1 | 1 | 0/4 | 4/4 | 0/4 | 0/4 |
| 1:2 | 0.5 | 1/4 | 4/4 | 1/4 | |
| 1:4 | 0.25 | 1/4 | 4/4 | 2/4 | |
| 1:8 | 0.125 | 1/4 | 4/4 | 2/4 | |
| 1:16 | 0.0625 | 2/4 | 4/4 | 3/4 | |
| 1:32 | 0.03125 | 4/4 | 4/4 | 4/4 | |

It can be seen from calculation in table 7 that the tectorigenin derivative with a concentration of 0.976 mg/ml has an inhibiting effect on coronavirus.

The conclusions are as follows:

TABLE 8

Summarized table of the tectorigenin derivative toxicity to Vero E6 cell and its coronavirus-inhibiting effect

| Drug designation | $TD_{50}$ (mg/ml) | $IC_{50}$ (mg/ml) |
|---|---|---|
| Compound IV | 4.34 | 0.0976 |
| Compound V | 4.52 | 0.0968 |
| Compound VI | 3.85 | 0.1200 |
| Compound VII | 4.20 | 0.1015 |
| Compound VIII | 3.45 | 0.1120 |
| Compound IX | 2.89 | 0.1251 |
| Compound X | 3.95 | 0.1187 |

The above-mentioned test results demonstrate:

① Toxicity of the tectorigenin derivative in the invention to Vero-E6: the tectorigenin derivative is added into Vero-E6 cell, the latter is cultivated for five says, when the cell pathologic change is taken as an index its median toxic concentration (TD50) is 2.34 mg/ml and maximum nontoxic concentration (TD0) is 1 mg/ml.

② The tectorigenin derivative has an inhibiting effect on coronavirus in Vero-E6 cell: the tectorigenin derivative injection is added into Vero-E6 cell, which is cultivated for five days, its median effect concentration (IC50) is 0.0976 mg/ml and the tectorigenin derivative injection minimum therapeutic index for coronavirus is 23.98.

(5) The Avian Influenza H5N1-&-H9N2 Subtype Virus-killing Effect Test

The following is in vitro avian influenza virus (AIV)-killing test in the case of taking the tectorigenin derivatives mentioned in the above examples as a test drug.

(5.1) Materials and Method

① Tested Drug

The tectorigenin derivative solution in the above examples (a faint yellow liquid containing 30 mg raw drug per ml).

② Avian Influenza Virus

The virus strain is A/Goose/Guandong/1/96(H5N1) and A/Chicken/Shangdong/6/96(H9N2), stored in the Agricultural Ministry's Key Animal Influenza Open Laboratory relied on Harbin Veterinary Medicine Research Institute subordinated to Chinese Academy of Agricultural Science.

③ Chick Embryo

The 10 days-aged SPF chick embryos, provided by the experimental animal center of Harbin Veterinary Medicine Research Institute subordinated to Chinese Academy of Agricultural Science.

④ Preparatory Test a. Virus EID50 Measurement

The avian influenza viruses subtype H5 and H9 are diluted in a 10-fold series, vaccinated in the 10 days-aged SPF chick embryos, each dilution is for five embryos (0.1 ml/embryo) and the virus median infection dose (EID50) is measured.

b. The Tested Drug Mother Liquor Modulation

The above-mentioned tectorigenin derivatives are taken as the mother liquor containing 30 mg raw drug per ml.

c. The Tested Drug's Maximum Nontoxic Dose for Chick Embryos 30 mg, 15 mg, 7.5 mg, 3.75 mg, 1.875 mg, 0.9375 mg, 0.46875 mg, 0.234375 mg and 0.1171875 mg per ml solutions of the tested raw drug are vaccinated in the 10 days-aged SPF chick embryos respectively and the solution with the first dilution is vaccinated in five chick embryos (0.1 ml/embryo). The vaccinated chick embryos are placed in a thermostat at 37° C. to be cultivated for 96 hours. The chick embryos died in 24 hours are discarded and their death is recorded.

⑤ The Tested Drug's Virus-kill Rate Test

A killing test of two (a strong and a weak) avian influenza viruses is carried out by the tested drug by use of Klein-Dofors suspension method, the tested drug is diluted in a 10-fold series by sterilized physiological saline and vaccinated and the infected chick embryos are checked.

a. Virus Suspension Preparation

The avian influenza viruses subtype H5 and H9 are made into 107.63 EID50/0.1 ml and 108.17 EID50/0.1 ml virus suspensions.

b. The Tested Drug Mother Liquor Modulation

The above-mentioned tectorigenin derivatives are diluted with sterilized physiological saline to a necessary concentration as a raw material during the killing test.

c. Klein-Dofors Suspension Killing Test 107.63 EID50 avian influenza subtype H5 virus suspension and 108.17 EID50 H9 subtype virus suspension are mixed with the tectorigenin derivatives with concentration of 30 mg, 15 mg, 7.5 mg, 3.75 mg, 3.0 mg, 1.875 mg, 1.5 mg, 0.75 mg and 0.375 mg raw drug per ml in a ratio 1: 9 respectively and diluted progressively by 10 times by use of sterilized physiological saline after reaction for five minutes at 20±1° C. The similar treatment is conducted by the substitution of the sterilized physiological saline for the sterilized virus suspension in the control group; the diluted solution is vaccinated the 10 days-aged chick embryos and the solution with each concentration is vaccinated in five chick embryos (0.1 ml/embryo). The vaccinated chick embryos are kept in an incubator at 37° C. for cultivation and the chick embryos death is recorded. The chick embryos died in 24 hours are discarded, the chick embryos died after 24 hours are taken out, all the chick embryos are taken out in 96 hours, their allantoic fluid is sampled one by one for HA test and the chick embryo which is proved to be positive by HA test is judged as infected one.

The chick embryo infection positive rate, EID50 content in samples and kill rate in the test and control groups are calculated according to the chick embryo infection result and the following equation.

Positive rate=quantity of the HA test-proven positive chick embryos/quantity of the vaccinated chick embryos;

logarithm of the EID content in samples=L-d (S-0.5)

(L is a logarithm of the minimum dilution multiple; d is a logarithmic difference between dilutions; S is a sum of the positive rates in each dilution column.)

Virus kill rate=(EID50 content in control samples-EID50 content in test samples/EID50 content in control samples× 100%)

(5.2) Test Result

① The Tested Drug Maximum Nontoxic Dose for Chick Embryos

The tectorigenin derivative diluted with sterilized physiological saline and containing 30 mg, 15 mg, 7.5 mg, 3.75 mg, 1.875 mg, 0.9375 mg, 0.46875 mg, 0.234375 mg and 0.1171875 mg raw drug per ml is injected in the chick embryos, the test result demonstrates that the drug with different concentration does not cause the chick embryos die after injection and this indicates that the tested drug original solution and the drug with its different concentration have no visually toxic effect on the chick embryos. The result is shown in table 9.

TABLE 9

The tested drug maximum nontoxic dose for chick embryos

| | Different concentrations of the tectorigenin derivatives, mg/ml | | | | | | | | |
|---|---|---|---|---|---|---|---|---|---|
| | 30 | 15 | 7.5 | 3.75 | 1.875 | 0.938 | 0.469 | 0.234 | 0.117 |
| Chick embryo death | 0/5 | 0/5 | 0/5 | 0/5 | 0/5 | 0/5 | 0/5 | 0/5 | 0/5 |

Note: the numerator is the quantity of died embryos and the denominator is the quantity of vaccinated embryos.

② The Tested Drug Killing Effect on Avian Influenza Virus

The tectorigenin derivative diluted with sterilized physiological saline and containing 30 mg, 15 mg, 7.5 mg, 3.75 mg, 3.0 mg, 1.875 mg, 1.5 mg, 0. 75 mg, and 0.375 mg per ml reacts with 107.63 EID50 avian influenza H5 subtype virus solution for five minutes, its virus-killing rate is measured respectively, the tectorigenin derivative with different dilution concentration reacts with 108.17 EID50 avian influenza virus type H9 for five minutes and its virus-killing rate is measured respectively. The result is shown in table 10.

TABLE 10

Killing effect of the tectorigenin derivative with different concentration on subtype H5N1 and H9N2 viruses

| Sample | Virus designation | The tectorigenin derivative, mg/ml | | | | | | | | |
|---|---|---|---|---|---|---|---|---|---|---|
| | | 30 | 15 | 7.5 | 3.75 | 3.0 | 1.875 | 1.5 | 0.75 | 0.375 |
| Compound IV | H5 subtype | 100% | 99.99% | 99.99% | 99.99% | 93.23% | 32.39% | 32.39% | 0 | 0 |
| | H9 subtype | 100% | 100% | 99.99% | 99.99% | 99.00% | 68.37% | 32.39% | 0 | 0 |
| Compound V | H5 subtype | 100% | 99.99% | 99.99% | 99.99% | 92.53% | 32.40% | 32.40% | 0 | 0 |
| | H9 subtype | 100% | 100% | 99.98% | 99.98% | 98.60% | 67.35% | 31.69% | 0 | 0 |

TABLE 10-continued

Killing effect of the tectorigenin derivative with different concentration on subtype H5N1 and H9N2 viruses

| Sample | Virus designation | The tectorigenin derivative, mg/ml | | | | | | | | |
|---|---|---|---|---|---|---|---|---|---|---|
| | | 30 | 15 | 7.5 | 3.75 | 3.0 | 1.875 | 1.5 | 0.75 | 0.375 |
| Compound VI | H5 subtype | 95.98% | 95.98% | 95.98% | 95.98% | 91.50% | 29.32% | 39.32% | 0 | 0 |
| | H9 subtype | 96.99% | 96.99% | 96.99% | 96.99% | 94.55% | 58.37% | 28.39% | 0 | 0 |
| Compound VII | H5 subtype | 99.87% | 99.87% | 99.87% | 99.87% | 92.30% | 45.19% | 45.19% | 0 | 0 |
| | H9 subtype | 99.25% | 99.25% | 99.25% | 99.25% | 98.00% | 58.31% | 28.85% | 0 | 0 |
| Compound VIII | H5 subtype | 99.56% | 99.56% | 99.56% | 99.56% | 91.13% | 30.30% | 30.30% | 0 | 0 |
| | H9 subtype | 99.69% | 99.69% | 99.69% | 99.69% | 94.00% | 65.34% | 32.19% | 0 | 0 |
| Compound IX | H5 subtype | 95.21% | 95.21% | 95.21% | 95.21% | 92.41% | 30.52% | 30.52% | 0 | 0 |
| | H9 subtype | 98.20% | 98.20% | 96.41% | 96.41% | 93.00% | 41.41% | 31.39% | 0 | 0 |
| Compound X | H5 subtype | 98.96% | 98.96% | 98.96% | 98.96% | 91.01% | 28.69% | 28.69% | 0 | 0 |
| | H9 subtype | 99.95% | 100% | 99.99% | 99.99% | 99.00% | 68.37% | 32.39% | 0 | 0 |

The above-mentioned test result indicates that the tested drug's killing effect on avian influenza virus is studied by use of Kein-Defors suspension killing and infection test method in the case of in vitro direct contact of the tectorigenin derivative (with different concentration) with the avian influenza viruses H5N1 and H5N2 (9:1) for five minutes respectively. The result demonstrates that the tectorigenin derivative containing 3.0 mg raw drug per ml has a certain virus-killing effect when it acts on the avian virus for five minutes, the tectorigenin derivative containing 3.75~30 mg raw drug per ml has an excellent virus-killing effect and its virus-killing rate could reach over 95% when it acts on the avian influenza virus for five minutes.

Its safety test indicates that vaccination of a series of mother liquor diluents in chick embryos does not cause the chick embryos die and this shows that variously diluted drugs of the tested drug mother liquor and original liquor have no visually toxic effect.

INDUSTRIAL APPLICATION

The tectorigenin compound derivative achieved by chemical modification in the invention as shown in formula (II) can greatly increase its water-solubility and chemical stability under the precondition of maintaining the antiviral and anti-inflammatory effects equivalent to those of its precursor material, i.e. the originally extracted tectorigenin compound, its preparation is simple, cost is low, it is safe and reliable, any special equipment is unnecessary and there is no pollution caused by "The three wastes" (i.e. the waste gas, waste water and industrial residue). Since constituents of the traditional Chinese medicine are complicated and it is difficult to control its quality stability, the isoflavone derivatives of tectorigenin compound provided by this invention have an important positive significance and a bright development prospect in respect of expanding its pharmaceutical and clinical application scope and especially in respect of the antiviral and anti-inflammatory injection preparation.

The above detailed description about this invention is not limited in this invention, the technicians in this field can make various modifications and changes on the basis of this invention and they should all belong to the claims attached in this invention, provided they do not digress from the spirit of this invention.

The invention claimed is:

1. A compound or a pharmaceutically acceptable salt thereof having formula (VI):

2. A compound as described in claim 1, wherein said compound is a pharmaceutically acceptable salt thereof.

3. The compound as described in claim 2, wherein said salt is hydrochloride.

4. A compound or a pharmaceutically acceptable salt thereof having formula (VII):

5. A compound or a pharmaceutically acceptable salt thereof having formula (VIII):

(VIII)

(IX)

6. A compound as described in claim 5, wherein said compound is a pharmaceutically acceptable salt thereof.

7. The compound as described in claim 6, wherein said salt is hydrochloride.

8. A compound or a pharmaceutically acceptable salt thereof having formula (X):

9. A compound as described in claim 8, wherein said compound is a pharmaceutically acceptable salt thereof.

10. The compound as described in claim 9, wherein said salt is hydrochloride.

* * * * *